April 20, 1965 W. E. LAMMERTS Plant Pat. 2,493
ROSE PLANT
Filed Feb. 17, 1964
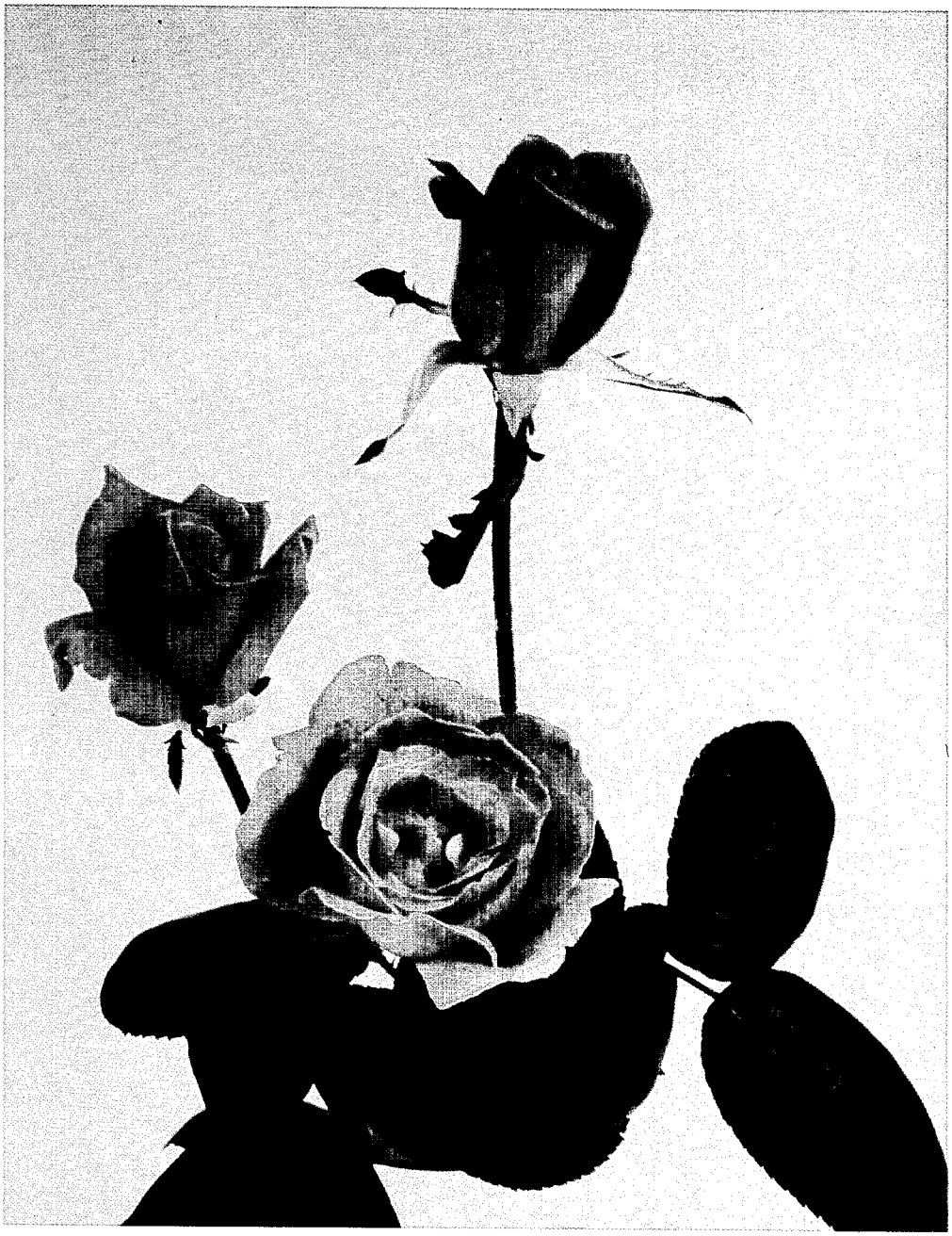
Inventor.
Walter E. Lammerts
By: Robb & Robb
Attorneys.

United States Patent Office

Plant Pat. 2,493
Patented Apr. 20, 1965

2,493
ROSE PLANT

Walter E. Lammerts, Livermore, Calif., assignor to Germain's, Inc., Los Angeles, Calif., a corporation of California Filed Feb. 17, 1964, Ser. No. 345,545
1 Claim. (Cl. Plt.—20)

The present invention relates to a new and distinct variety of rose plant of the hybrid tea class, which was originated by me by crossing the variety "Charlotte Armstrong" (Plant Patent No. 455) with the variety "Merry Widow" (Plant Patent No. 1,711).

As the result of this breeding, I have produced a new and improved rose variety which is endowed with a unique combination of outstanding characteristics which distinguish the new variety from its parents, as well as from all other varieties of which I am aware, as evidenced by the following principal features:

(1) Vigorous, tall, upright and compact habits of growth;

(2) A habit of bearing its flowers usually singly and on long and strong cutting stems;

(3) Long pointed buds with clasping sepals, said buds being basically Scarlet in color, with a Dark Canary Yellow base;

(4) A distinctive and attractive open flower form in which the lower portions of the inner petals extend vertically upward, while the upper portions are more horizontal and arch outward from the center but cover the central stamen and pistil area until the flower ages, thereby giving the appearance of greater petalage;

(5) A distinctive and attractive Scarlet general color tonality of the flowers which is retained without blueing as the flowers age; and (6) An intense flower fragrance reminiscent of *R. centifolia* varieties even during dry weather and under other adverse conditions.

The new variety has a taller, more upright and compact habit of growth than the parent variety "Charlotte Armstrong," and in this respect, resembles the parent variety "Merry Widow." "Charlotte Armstrong" is a hybrid of "Soeur Therese" (unpatented) × "Crimson Glory" (Plant Patent No. 105), and is more upright in its growth habit than "Crimson Glory," but resembles it in being base-branching, with many canes growing at approximately 45° to 50° angles with relation to the ground. Accordingly, it has a tendency toward a spreading habit of growth. By contrast therewith, even the new basal canes of my new variety quickly curve upward as they begin to grow, with the canes extending at angles of approximately 75° to 90° in relation to the ground. As the result, the plant of my new variety is much more compact in its growth habit, thus taking up less space in the garden than such base-branching varieties as "Crimson Glory," "Sierra Glow" (Plant Patent No. 521), and even "Charlotte Armstrong."

Although the new variety is a hybrid tea with most of the flowers being borne singly on long and strong cutting stems, the habit and vigor compare favorably with the parent variety "Merry Widow," and it is more vigorous than "Charlotte Armstrong" in respect to both height and total growth. The foliage, thorns and other plant characteristics are otherwise quite similar to those of "Charlotte Armstrong."

While the buds of my new variety are similar to those of "Charlotte Armstrong," particularly in respect to their long pointed form, with clasping sepals, the basic color of the buds of the new variety is more Scarlet because of their Dark Canary Yellow base color. The open flower is also generally similar to that of "Charlotte Armstrong" in size, form and color, but the color is more Scarlet in general color tone. The inner petals have the same arching tendency as the flowers of "Charlotte Armstrong," which gives the impression of greater petalage, although the flowers actually have only from 25 to 35 petals.

The newly open flower of the new variety is also more Scarlet than that of "Charlotte Armstrong," and therefore does not tend to blue or show as much magenta coloration with age.

The most distinctive characteristic of the new variety is its intense flower fragrance which is reminiscent of the older *R. centifolia* varieties. It is much more fragrant than "Merry Widow" or even "Chryster Imperial" (Plant Patent No. 1,167). Accordingly, it corrects what undoubtedly is a fault in "Charlotte Armstrong," which, at its best, has only a slight, rather delicate fragrance which is dependent for its expression on conditions of optimum humidity and temperature. Even under the driest and most adverse conditions, my new variety is intensely fragrant, and a pleasing old-fashioned rose perfume is easily noted in the average living room even when only one newly opened flower of the new variety is displayed in the room.

Asexual reproduction of my new variety by budding, as performed by me at Livermore, California, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with the Horticultural Colour Chart of the British Colour Council, except where general color terms of ordinary dictionary significance are obvious, as based upon observations of specimens grown at Livermore, California:

Type: Half hardy; tall; bush; outdoor; seedling; for garden decoration.
Class: Hybrid tea.
Breeding: Seedling.
*Seed parent.*—"Charlotte Armstrong."
*Pollen parent.*—"Merry Widow."
Propagation: Holds its distinguishing characteristics through succeeding propagations by budding.

*Flower*

Flowers borne: Singly; on strong, long stems of medium length.
Quantity of bloom: Free, outdoors.
Continuity: Continuous.
Fragrance: Strong. Nature—centifolia.
Bud:
*Peduncle.*—Medium length; slender; medium caliper; erect; few very small prickles. Color—light green.
*Before calyx breaks.*—Size—medium large. Form—long; pointed; with 2 or 3 lance shaped appendages from ⅛ inch to ¼ inch long on sides of every other sepal which also have foliaceous parts extending beyond the tip of the bud equal to ¼ of its length. Color—Cardinal Red, Plate 822/1.
*As calyx breaks.*—Color—from Cardinal Red, Plate 822/1 to Cherry, Plate 722.

*As first petal opens.*—Size—medium large. Form—long; pointed. Color: Outside—Scarlet, Plate 19/1 near base of petal, shading to Tyrian Rose, Plate 24/1 on upper portion of petal; inside—from Crimson, Plate 22 to Tyrian Rose, Plate 24/1.

*Opening.*—Opens up well; is retarded from opening by cold, wet or dry weather.

Bloom:

*Size (when fully open).*—Medium large; from 4 inches to 5 inches.

*Petalage.*—Double; from 25 to 35 petals.

*Form.*—High-centered at first, then opening to regularly imbricate but somewhat loosely arranged petals, with the central petals remaining clustered and at right angles to the plane of the flower so that the anthers are usually covered; petals being at first very tightly rolled inward, but later becoming rolled outward at maturity.

Petals:

*Texture.*—Thin; soft.

*Appearance.*—Inside—satiny. Outside—satiny.

*Shape.*—Outside—obovate, often with slight apex ranging from 1/16 inch to 1/8 inch long. Intermediate—obovate, with apex having no notches. Inside—obovate, with apex having no notches.

This description of a newly opened flower was made from a rose grown outdoors during the month of October at Livermore, California:

*Color.*—Outer petal: outside surface—Canary Yellow, Plate 2/1 at base, shading to between Scarlet, Plate 19/2 and Carmine, Plate 21/1; inside surface—Canary Yellow, Plate 2 at base, shading to between Scarlet, Plate 19/1 and Rose Madder, Plate 23/1. Intermediate petal: outside surface—Canary Yellow, Plate 2/1 at base, shading to between Scarlet, Plate 19/2 and Carmine, Plate 21/1; inside surface—Canary Yellow, Plate 2 at base, shading to between Scarlet, Plate 19/1 and Rose Madder, Plate 23/1. Inner petal: outside surface—Canary Yellow, Plate 2/1 at base, with remainder of petal Crimson, Plate 22/1; inside surface—Canary Yellow, Plate 2 at base, remainder of petal Crimson, Plate 22.

This description was made from a rose that was open for three days outdoors during the month of October at Livermore, California:

*Color.*—Outer petal: outside surface—Rose Bengal, Plate 25/2; inside surface—Rose Bengal, Plate 25/1. Inner petal: outside surface—Rose Bengal, Plate 25/2; inside surface—Rose Bengal, Plate 25/1.

*General color effect.*—Newly opened flower—from Scarlet, Plate 19/2 to Rose Madder, Plate 23/1. 3 days open—Rose Bengal, Plate 25/2.

*Behavior.*—Drop off cleanly; affected by cold weather by becoming more Rose Bengal or even Solferino Purple colored.

*Flower longevity.*—On bush in garden—3 days in October. Cut roses grown outdoors and kept at living room temperatures—3 days in October.

*Reproductive organs*

Stamens: Many; arranged irregularly about pistils. Color—Majolica Yellow, Plate 09.

Filaments: Short; most with anthers. Color—yellow.

Anthers: Medium large; open at various times. Color—yellow.

Pollen: Moderate quantity. Color—gold.

Pistils: Many.

Styles: Uneven; some short to medium long; thin; rather tightly compacted. Color—upper portion Spirea Red, Plate 025, with basal portion Sulphur Yellow, Plate 1/2.

Stigma: Color—Sulphur Yellow, Plate 1/2.

Ovaries: All enclosed in calyx.

Hips: Pear-shaped. Color—Yellow.

Sepals: Permanent; medium long; spear-shaped; recurved. Color: inside—Willow Green, Plate 000862/2; outside—Spinach Green, Plate 0960/3.

Seeds: Many; medium large.

*Plant*

Foliage:

*Leaves.*—Compound of 5–7 leaflets; abundant; medium large; leathery.

*Leaflets.*—Shape—elongate oval, with apex acute. Base—round. Margin—doubly serrate.

*Color.*—Mature: upper surface—Parsley Green, Plate 00962; under surface—Sage Green, Plate 00861/1. Young: upper surface—lighter than Parsley Green, Plate 00962, with some anthocyanin pigment; under surface—lighter than Sage Green, Plate 00861/1, with some anthocyanin pigment.

*Rachis (the supporting stem of the compound leaf).*—Medium heavy. Upper side—smooth; grooved. Under side—sparsely prickly.

*Stipules.*—Short; narrow; with short points turning out at an angle of 45°.

*Disease resistance.*—Good resistance to mildew, as determined by comparison with other varieties grown under comparable cultural conditions at Livermore, California.

Growth:

*Habit.*—Tall; upright; compact.

*Growth.*—Vigorous.

*Canes.*—Heavy.

*Main stems.*—Color—dull grey green. Thorns—many; medium long; hooked downward; with long narrow base. Prickles—few; color—grey green. Hairs—none.

*Branches.*—Color — dull grey green. Thorns—many; medium long; hooked downward; with long narrow base. Prickles—few; color—grey green. Hairs—none.

*New shoots.*—Color—dull grey green, tinged slightly with bronze. Thorns—many; medium long; hooked downward; with long narrow base. Prickles—few; color—grey green. Hairs—none.

I claim:

A new and distinct variety of rose plant of the hybrid tea class, substantially as herein shown and described, characterized particularly as to novelty by the unique combination of vigorous, tall, upright and compact habits of growth, a habit of bearing its flowers usually singly on long and strong cutting stems, long pointed buds with clasping sepals, said buds being basically Scarlet in color, with bases of Canary Yellow, a distinctive and attractive open flower form in which the lower portions of the inner petals extend vertically upward, while the upper portions are more horizontal and arch outward from the center but cover the central stamen and pistil area until the flower ages, thereby giving the impression of greater petalage, a distinctive and attractive Scarlet general color tonality of the flowers which is retained without blueing as the flowers age, and an intense flower fragrance reminiscent of *R. centifolia* varieties even under conditions of dry weather and other adverse conditions.

No references cited.

T. GRAHAM CRAVER, *Primary Examiner.*